US006969605B2

(12) United States Patent
Anderson et al.

(10) Patent No.: US 6,969,605 B2
(45) **Date of Patent: *Nov. 29, 2005**

(54) MINIATURE IMMUNO-OPTICAL RAPID ANALYTE SENSOR PLATFORM

(75) Inventors: Charles W. Anderson, Woodbine, MD (US); C. Brent Bargeron, Columbia, MD (US); Richard C. Benson, Highland, MD (US); Micah A. Carlson, Baltimore, MD (US); Allan B. Fraser, Woodbine, MD (US); John D. Groopman, Owings Mills, MD (US); Harvey W. Ko, Ellicott City, MD (US); David R. Kohler, Ellicott City, MD (US); Terry E. Phillips, Ellicott City, MD (US); Paul T. Strickland, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 753 days.

This patent is subject to a terminal disclaimer.

(21) Appl. No.: 09/906,243

(22) Filed: Jul. 16, 2001

(65) Prior Publication Data

US 2001/0053556 A1 Dec. 20, 2001

Related U.S. Application Data

(63) Continuation of application No. 09/074,644, filed on May 8, 1998, now Pat. No. 6,261,848.

(51) Int. Cl.[7] .............................................. C12M 3/00

(52) U.S. Cl. .............................. 435/287.1; 210/198.2; 210/656; 210/659; 250/458.1; 250/459.1; 250/461.1; 250/462.1; 422/56; 422/69; 422/70; 435/287.2; 435/288.5; 435/288.7; 436/161; 436/172; 436/518; 436/529; 436/530; 436/531; 436/534; 436/536

(58) Field of Search ............................ 210/198.2, 656, 210/659; 250/458.1, 459.1, 461.1, 462.1; 422/56, 69, 70; 435/287.1, 287.2, 288.5, 435/288.7; 436/161, 172, 518, 529, 530, 436/531, 534, 536

(56) References Cited

U.S. PATENT DOCUMENTS 3,744,219 A 7/1973 Tindle et al.

(Continued)

OTHER PUBLICATIONS

Thomas et al. Determination of Alrazine in Water Using Tandem High-performance immunoaffinity Chromatography and Reversed-Phase Liquid Chromatography. Anal. Chem. 66:3823-3829. Nov. 1, 1994.

(Continued)

*Primary Examiner*—Christopher L. Chin
(74) *Attorney, Agent, or Firm*—Francis A. Cooch

(57) ABSTRACT

A hand held, self-contained, automatic, low power and rapid sensor platform for detecting and quantifying a plurality of analytes. A sample solution potentially containing an unknown amount of an analyte is passed through an affinity column which contains antibodies to which the analyte binds thereby extracting the analyte. The affinity column is then rinsed to remove any other chemicals that may fluoresce. The rinsed affinity column is then eluted with a known volume of elution fluid causing the analyte to release from the antibody and dissolve in the fluid (eluant). The eluant is then placed in the quartz cuvette of a fluorometer. The analyte suspended in the eluant fluoresces at a waveband which is different than that of the light source that excites it. The amount of fluorescence is measured and the level of analyte determined. The rinsing and elution fluids, and/or the affinity column can be placed in a module for easy insertion and removal from the sensor when depleted or when the sensor is to be used against a different analyte.

34 Claims, 2 Drawing Sheets

U.S. PATENT DOCUMENTS 4,802,981 A 2/1989 Kenney et al.
4,861,488 A 8/1989 Kenney et al.
4,937,200 A 6/1990 Kumazawa et al.
5,074,977 A 12/1991 Cheung et al.
5,205,291 A 4/1993 Potter
5,328,603 A 7/1994 Velander et al.
5,340,543 A 8/1994 Annino et al.
5,399,866 A 3/1995 Feldman et al.
5,487,998 A 1/1996 Umrigar et al.
5,491,096 A 2/1996 Sportsman
5,491,344 A 2/1996 Kenney et al.
5,834,318 A 11/1998 Buettner
6,261,848 B1 * 7/2001 Anderson et al. ........... 436/518

OTHER PUBLICATIONS

Ruhn et al. Determination of Urinary Albumin Using High-Performance Immunoaffinity Chromatography and Flow Injection Analysis. Anal. Chem. 66:4265-4271. Dec. 1, 1994.

Carman et al. Robotic Automated Analysis of Foods for Aflatoxin. Journal of AOAC International 79(2):456-464. Mar.-Arp. 1996.

* cited by examiner

MINIATURE IMMUNO-OPTICAL RAPID ANALYTE SENSOR PLATFORM

CROSS-REFERENCE TO RELATED APPLICATION

This application is a continuation of application Ser. No. 09/074,644, filed May 8, 1998, now issued as U.S. Pat. No. 6,261,848, on Jul. 17, 2001.

STATEMENT OF GOVERNMENTAL INTEREST

This invention was made with Government support under Contract No. MDA972-96-D-0002 awarded by the Defense Advanced Research Projects Agency. The Government has certain rights in the invention.

BACKGROUND OF THE INVENTION

The invention relates in general to sensors and, more particularly, to a hand held, self-contained, automatic, low power and rapid sensor platform for detecting a plurality of analytes.

While the invention can be used to detect a wide variety of analytes, the initial embodiment was developed for use against aflatoxin which is formed from a fungus commonly found in many grain products and peanuts. Studies have proven that ingesting aflatoxin can cause serious health problems. The FDA is aware of this health risk and has set tolerance levels for aflatoxin for United States products such as flour and milk.

However, high levels of aflatoxin do still exist in food in remote areas and foreign countries, where it is also used in weaponry. It is these unacceptable levels in food and the potential use in weapons that have prompted investigations into a portable sensor for aflatoxin and, by extension, to other analytes of interest as well.

There currently exist two different measurement techniques for aflatoxin levels. The easiest and most portable method uses a paper that changes color when immersed in a minimum concentration of aflatoxin. Currently available test papers are for minimum levels of 5 parts per billion (ppb) and 20 ppb.

The second, less portable method of measuring aflatoxin levels uses affinity chromatography and a series of manual fluid currently available uses a "wet chemistry" approach. This method uses a paper that changes color when immersed in a minimum concentration of aflatoxin. Currently available test papers are for minimum levels of 5 parts per billion (ppb) and 20 ppb.

The second, less portable method of measuring aflatoxin levels uses affinity chromatography and a series of manual fluid wash and rinse cycles that effectively selectively remove the aflatoxin from the initial sample solution. The aflatoxin, contained in the final rinse (elution) fluid, may then be placed in a fluorometer where its fluorescence can be measured and correlated to the level of aflatoxin in the initial sample.

Despite the existence of the above techniques, a need remains for a hand held, self-contained, automatic sensor with increased sensitivity to replace the less sensitive "wet chemistry" method and the large, cumbersome, chemical laboratory analysis systems. The new sensor should be viable for use not only against aflatoxin but against other analytes of agricultural, public health and defense interest as well. A modular design permitting the rapid substitution of different reagents and/or affinity columns to permit detection of various analytes with the same sensor would provide even greater benefits.

SUMMARY OF THE INVENTION

The sensor of the invention solves the above problems by offering the following important advantages: it is hand held, self-contained, automatic, low power, highly sensitive and selective, quantitative, stable with a long shelf-life, and fast (<2 min). It can be used against many different analytes with the reagents and/or affinity column appropriate for each analyte being inserted and removed as a single, modular unit.

The invention operates on the principles of immuno-affinity for specificity and fluorescence for a quantitative assay. It comprises two principal subsystems: a fluidic and chemical system that concentrates the analyte on an affinity column and elutes the concentrate into a small volume, and a sensitive fluorometer that measures the concentrated analyte's natural fluorescence. Both subsystems are located in the hand held, enclosed container that comprises the sensor of the invention. In one embodiment, the sensor can measure the concentration of aflatoxin in aqueous solution to concentrations down to 0.1 ppb.

After the sensor's built-in power supply is turned on, the user places a syringe with the sample solution in the sensor's external port and injects enough sample to clear bubbles through a bubble release valve. The operation of the sensor thereafter is entirely automatic, controlled by an on-board microcontroller. The intake of the sample and the clearing of bubbles through the bubble release valve could be automated as well.

The injected sample solution is drawn through an affinity column, which binds the analyte with great specificity. Next, a rinse fluid is drawn through the affinity column to wash it of any dissolved or suspended material that may later interfere with the fluorometric assay. The affinity column is, thus, washed clean, except for the chemically bound analyte. Next, a small, known quantity of elution fluid is drawn through the affinity column. This step releases the analyte, which is delivered in the elution fluid or eluant to a fluorometric cuvette.

The electro-optical subsystem or fluorometer is activated to measure the natural fluorescence of the analyte. A xenon arc lamp, run in single pulse mode, is used in the aflatoxin sensor embodiment of the invention as the radiation source. The arc lamp makes a flash on the order of a microsecond and radiation from the flash is captured by a first optical system or lens and is filtered by a UV filter to remove all light but a band in the near ultraviolet that excites aflatoxin fluorescence. The near ultraviolet light is then focused onto and transmitted through the fluorometric cuvette, and blue fluorescent light is emitted omnidirectionally by aflatoxin in the cuvette.

Some of the aflatoxin fluorescence leaving near 90° to the ultraviolet light path is captured by a second optical system and a second filter that passes only the blue fluorescent light emitted by the aflatoxin. The second optical system includes one or more lenses for focusing the fluorescent light from the cuvette on a detector, e.g., a photomultiplier tube (PMT).

The PMT, when illuminated by the blue fluorescent light, together with a the receiver circuit, measures aflatoxin based on the fluorescent energy from a single pulse of excitation. A transducer in the PMT produces on the order of a microsecond-long pulse of electrical current whose total charge is proportional to its light input, i.e., to the light generated by fluorescence in the sample, and, therefore, to the aflatoxin concentration.

In the receiver circuit, the PMT output drives a first operational amplifier circuit wired as a transimpedance amplifier with a low pass characteristic that is very long compared to the duration of the light pulse and the duration of the electromagnetic interference of the arc lamp. The transimpedance amplifier converts the charge (integral of the photocurrent) from the PMT into a decaying exponential pulse with amplitude and area both directly proportional to the charge from the PMT.

The output of the transimpedance amplifier is input to a track/hold circuit that is configured to make an output that tracks its input if an internal switch is in its normally closed condition. If the switch is placed in the open condition, the track/hold circuit holds the voltage at its output that was present immediately prior to the switch being opened. The track and hold circuit is switched into hold mode at the time that its output amplitude is the maximum in response to a pulse from the PMT.

The track/hold circuit reaches a peak response at a time long after a signal pulse comes from the PMT and the peak signal comes from the transimpedance amplifier. The track/hold circuit is placed in its hold mode also long after the pulse from the arc lamp occurred, and the track/hold circuit's output is directly proportional to the fluorescent light generated. Thus, the sensor output is decoupled from any electromagnetic interference generated by the sensor. While the hold condition is initiated at the time calculated for the peak signal, other times near that time would provide nearly equivalent results.

The track/hold circuit output/held value, i.e., the fluorescence intensity, is applied to the input to a digitizer/numerical display to be digitized and displayed to the operator of the instrument. Finally, after measurement is complete, the cuvette and plumbing are washed and backflushed and the system turns itself off.

If, unlike aflatoxin, the analyte to be detected does not have a measurable natural fluorescence, then a fluorescent tag can be added. For example, when the eluant leaves the affinity column, the eluant would be mixed with, depending on the analyte of interest, a fluorescent tag, e.g., a fluorescent tagged compound such as a peptide, or a "developer" to create the fluorescent tag. In addition, there could be a mixing means, such as a baffle, e.g., a screen, at the entry to the fluorometer. Also, depending upon the reaction rate, the mixed solutions could reside in the fluorometer for a specified time before the fluorescence measurement was made.

The invention utilizes recent technology in miniaturized fluidics, electro-optical components, and electronics. The optics employ low scatter and low fluorescence techniques throughout, and the electronics employ noise-rejecting and interference-rejecting techniques. The invention's process time, at under two minutes, is shorter than that of its competitors, which are also less sensitive.

The invention's modular design permits the affinity column and/or the reagents, including a developer or fluorescent tag and/or a waste chamber to be located in their own container(s) thus permitting them to be easily replaced when depleted and/or to be exchanged for another column and/or reagents for use against a different analyte. The system will perform more than one hundred assays before its first servicing by replacement of the affinity column. As noted, the invention is hand held, even with enough reagents for over one hundred assays, and can be made smaller. The invention can be operated while held in the hand or from any surface on which it is placed.

The invention has applications in defense, agriculture and public health.

Accordingly, an object of the invention is to provide a portable, i.e., hand held, and self-contained sensor for use in detecting and quantifying multiple analytes.

Another object of the invention is a modular design to facilitate the replacement/exchange of the affinity column and/or reagents used in the sensor, thus, permitting the rapid changing of the sensor's analyte of interest.

Yet another object of the invention is a sensor of increased sensitivity to the analytes of interest.

A further object of the invention is to provide a simple-to-operate sensor which functions automatically once a sample solution is injected therein.

Still another object of the invention is to operate rapidly, i.e., under two minutes, from injection of a sample into the sensor until the amount of analyte in the sample is displayed.

Another object of the invention is to provide a hand held, self-contained, automatic fluorometer for use in detecting and quantifying multiple analytes.

Yet another object of the invention is a circuit for decoupling the electromagnetic interference generated in a fluorometer from the fluorometer's output and for providing a peak or near peak value representing such output.

Other objects and advantages of the invention will become apparent to those skilled in the art in the course of the following description.

DETAILED DESCRIPTION

The sensor of the invention comprises two principal subsystems: a fluidic and chemical system that concentrates the analyte on an affinity column and elutes the concentrate into a small volume, and a sensitive fluorometer that measures the concentrated analyte's natural fluorescence. In one embodiment, the sensor, which is currently approximately 9"×6"×2.5" in size, can measure the concentration of aflatoxin in aqueous solution to concentrations down to 0.1 ppb.

Figure 1:
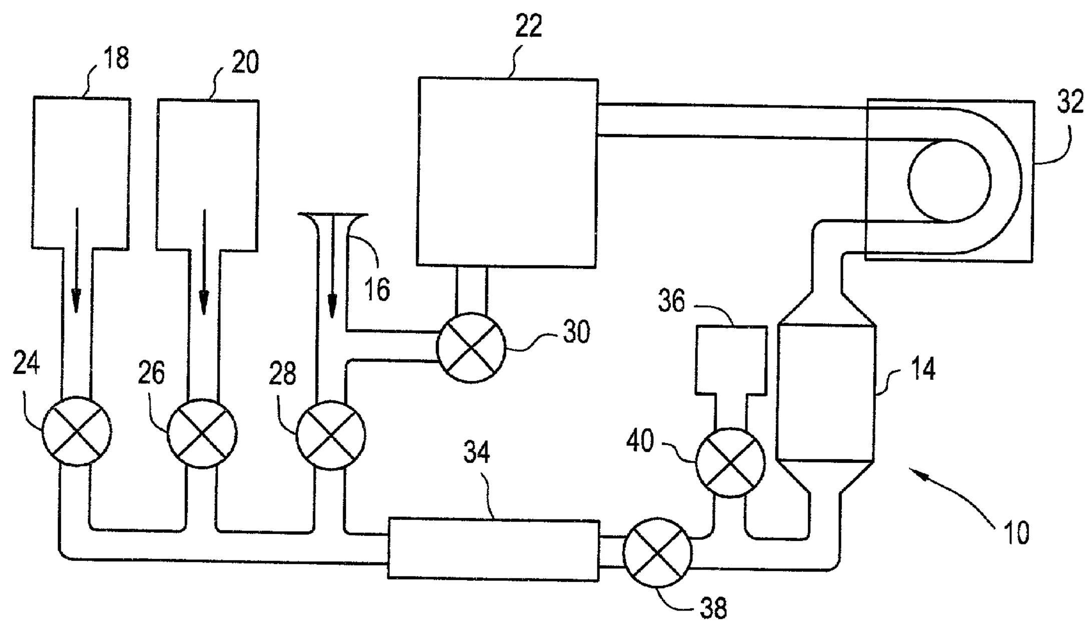
FIG. 1 illustrates the fluidic and chemical subsystem of the invention.
Figure 2:
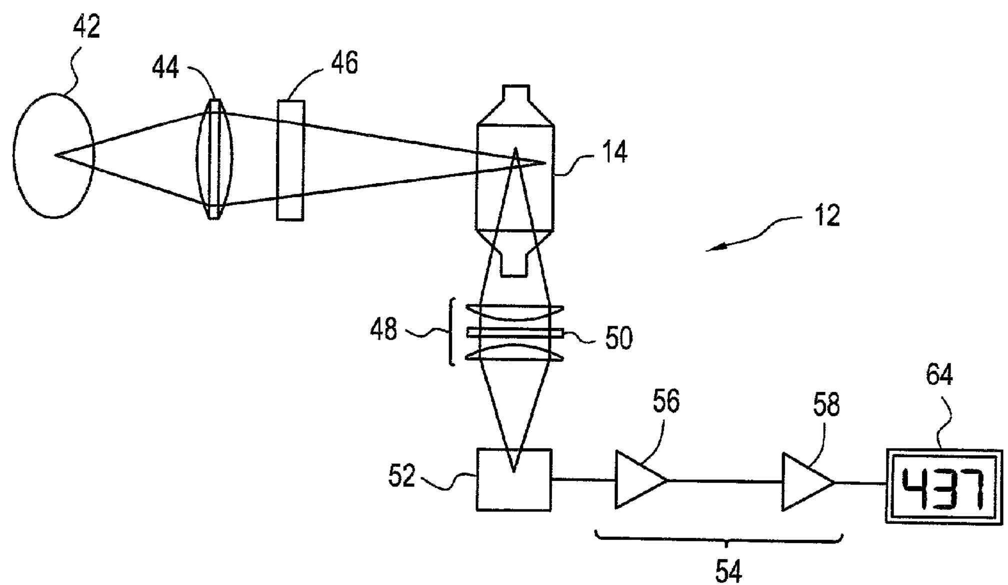
FIG. 2 illustrates the electro-optical, i.e., fluorometer, subsystem of the invention.

FIG. 1 illustrates the fluidic and chemical subsystem 10 of the invention while FIG. 2 illustrates the electro-optical fluorometer subsystem 12. The two subsystems intersect at the fluorometric cell 14, a cuvette, which is common to both figures. Operation of both subsystems and cues for the operator are managed automatically by an on-board microcontroller (not shown).

Turning to FIG. 1, in the aflatoxin sensor embodiment of the invention, the sample solution which may contain aflatoxin is prepared by the user from dry or aqueous starting materials and injected via a syringe at external port 16. First and second reservoirs 18, 20 containing a rinse fluid (e.g., a solution of clean buffered saline) and an elution fluid (e.g., buffered saline and methanol), respectively, and a waste chamber 22 are part of and located within the sensor. Sample sizes and solutions are minimal because the plumbing and the fluorometric cuvette are very small permitting the sensor to test multiple samples.

All materials used in the sensor were selected primarily on leeching characteristics and manufacturability. The materials need to exhibit minimal leeching to keep the background fluorescence to a minimum. Materials investigated included aluminum, stainless steel, titanium, scotch 3031, buna-n, delrin, polytetrafluoroethylene, isoplast, nylon, polyolefin, zellite, and polyvinyl chloride (PVC). Additional background readings were taken using silicone and platinum-cured silicone tubing, and methanol and phosphate buffered saline solutions.

Isoplast and platinum-cured silicone were used for their low leeching characteristics and for their manufacturability. The column (glass) and the cell (quartz) do not leech appreciably. Background fluorescence levels on the fluids also proved minimal (all were within the 0.1 ppb range). Higher levels of background fluorescence were seen due to the wetted valve materials and the molded scotch 3031.

The preliminary fluid movements were developed from research into potential sequences. Once this basic sequence was determined, the main driver of the fluid design became the multiple sample requirement. The valve type, size and placement were determined almost solely on the fluid movements needed to flush the system, especially the cuvette. Exhaustive testing was performed on several different designs using two and three-way valves in conjunction with open and closed systems.

The resulting invention is a closed system with four valves 24, 26, 28, 30 (aflatoxin sensor embodiment) that uses a relatively small volume (approximately 0.25 ml) cuvette 14. It is the small cuvette volume 14 that allows reduced valve sizes and pressures while keeping the test sequence within the time constraint. An example of suitable valves for the sensor of the invention are INKA-series two-way valves from the Lee Company for their size and power consumption rates.

Returning to FIG. 1, the peristaltic pump 32 drives fluids in the sensor from the first and second reservoirs 18, 20 and the external port 16 through an affinity column 34 and the fluorometric cuvette 14 to the waste chamber 22 under program (microcontroller) control. The peristaltic pump 32 is a positive displacement device, so all flows are managed, even when the instrument is inactive.

Several different pumping schemes were researched and evaluated. Manual fluid movement systems included: a simple syringe injection, a vacuum chamber, or a hand pump. Automatic fluid systems included: a series of motor-driven syringes, a fixed displacement pump, and a peristaltic pump. An example of a suitable pump for the sensor of the invention is the INSTEC Model P625 peristaltic pump based on its power consumption, size, cleanliness, accuracy and flexibility.

In embodiments of the invention where the analyte to be detected, unlike aflatoxin, does not have a measurable natural fluorescence, a third reservoir 36 containing a fluorescent tag, e.g., a fluorescent tagged compound such as a peptide, or a "developer" to create the fluorescent tag would be added as shown in FIG. 1. When an eluant left the affinity column 34 and reached the third reservoir 36, two valves 38, 40 would open and close alternately to mix the solutions. In addition, there could be a mixing means, such as a baffle (not shown), e.g., a screen, at the entry to the fluorometric cuvette 14. Depending upon the reaction rate, the mixed solutions could reside in the fluorometer for a specified time before the fluorescence measurement was made.

This general scheme would work for other mycotoxins like ochratoxin A, fumonisins (B1, B2, and B3), deoxynvalenol, and zearalenone by employing a developer that would derivatize the analyte to make it fluorescent. Enhanced aflatoxin B1 measurements could be achieved this way also by using its oxidant as the developer. Fluorescent tagged peptides would be used, for example, for botulism analyte or VAMP.

The operation of the invention begins with a sample solution potentially containing an unknown amount of the analyte of interest suspended in a saline reagent. After the sensor's built-in power supply (not shown) is turned on, the sample solution contained in a syringe is injected by the operator into the sensor at external port 16. Enough sample solution is used (0.2 ml minimum) to clear bubbles through the bubble release valve 30. The rest of the sensor operation is controlled by the on board microcontroller and is entirely automatic. The intake of the sample and the clearing of bubbles through the bubble release valve could be automated as well.

The basic form of analyte removal from the sample solution is to bind the analyte to antibodies attached to various microbead materials contained in the affinity column 34 (see, e.g., U.S. Pat. Nos. 5,491,068 and 4,859,611). An elution fluid from second reservoir 20 is then passed over the beads, causing them to release the analyte into solution.

Various bead materials, both magnetic and nonmagnetic, allow for different methods of extraction. Magnetic beads coated with antibodies can bind with the analyte and be easily mixed and removed from the sample fluid using a magnetic stirrer. However, bead life is a limiting factor.

Nonmagnetic beads can be placed in the affinity column 34 and the sample solution passed around them, exposing the analyte to the antibodies on the beads where binding occurs. The nonmagnetic column material (e.g., sepharose) with a 40-micron bead size was selected for its robustness and ease of use.

After being injected into the sensor, the sample solution is then passed through the affinity column 34 which, as noted above, contains antibodies to which the analyte in the sample solution binds. Thus, the antibody extracts the analyte from the sample. The affinity column 34 is rinsed with a phosphate buffered saline solution from first reservoir 18 to remove any other chemicals contained therein that may fluoresce.

The rinsed affinity column 34 is then eluted with a known volume of elution fluid from second reservoir 20. The elution fluid can vary but in the case of the aflatoxin sensor embodiment it is a 50/50 solution of phosphate buffer and methyl alcohol. The elution fluid causes the analyte to release from the antibody and dissolve in the fluid. This fluid, termed eluant, is then placed in the quartz fluorometric cuvette 14.

As noted above, if the analyte does not have a measurable natural fluorescence, then, when the eluant leaves the affinity column 34, two valves 38, 40 would be alternately opened and closed to mix the eluant with, depending on the analyte, a fluorescent tag, e.g., a fluorescent tagged compound such as a peptide, or a "developer" to create the fluorescent tag from third reservoir 36. In addition, there could be a mixing means, such as a baffle (not shown), e.g., a screen, at the entry to the fluorometric cuvette 14. Depending upon the reaction rate, the mixed solutions could reside in the fluorometer for a specified time before the fluorescence measurement was made.

Figure 3A:
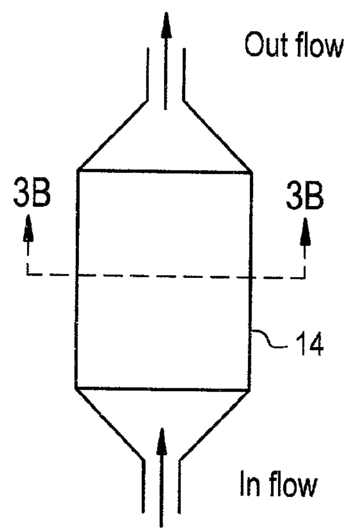
FIG. 3, consisting of FIGS. 3*a* and 3*b*, illustrates, in FIG. 3*a*, a side view of a quartz cuvette used in the fluorometer of the invention, and, in FIG. 3*b*, a cross sectional view of FIG. 3*a* taken along a—a.
Figure 3B:
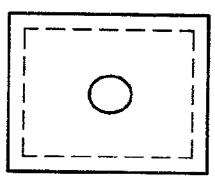

A flow-through cuvette is used in the invention. This style of cuvette, shown in FIG. 3, creates an easily flushed fluid path. The size and shape of the cuvette itself is related to the aperture needed for the fluorometer. The analyte suspended in the fluid fluoresces at a waveband which is different than that of the light source that excites it. The amount of fluorescence can then be measured and the level of analyte determined.

The fluorometric cuvette 14 with the potentially analyte-containing solution inside also appears on FIG. 2, which shows the electro-optical subsystem 12. The optics employ low scatter and low fluorescence techniques throughout, and the electronics employ noise-rejecting and interference-rejecting techniques.

The aflatoxin sensor embodiment of the invention requires a source of radiation that is both rich in near ultraviolet and energy efficient. These requirements lead to the selection of a xenon arc lamp 42, run in single pulse mode, as the excitation source/means of illumination.

As shown in FIG. 2, the xenon arc lamp 42 makes a flash on the order of a microsecond, and radiation from the flash is captured by a first optical system or lens 44. The arc lamp's radiation collected by the lens 44 is filtered by a UV or first filter 46 to remove all light but a band in the near ultraviolet that excites aflatoxin fluorescence. The near ultraviolet light is then focused onto and transmitted through the fluorometric cuvette 14, and blue fluorescent light is emitted omnidirectionally by aflatoxin in the cuvette.

Some of the aflatoxin fluorescence leaving near 90° to the ultraviolet light path is captured by a second optical system 48. Second optical system 48 includes one or more lenses for focusing the fluorescent light from the cuvette on a detector 52 and a second filter 50 that passes only the blue fluorescent light emitted by the aflatoxin.

The blue light illuminates a detector, e.g., a photomultiplier tube (PMT), 52 which, together with the receiver circuit 54, measures aflatoxin based on the fluorescent energy from a single pulse of excitation. The detector 52 and receiver circuit 54 have the following characteristics, among others:

1. make an output whose amplitude is proportional to the integral of the fluorescent light produced;
2. have low self noise and offset; and
3. have great rejection of the power transients and electromagnetic interference caused by the very close and highly energetic lamp pulse.

The detector 52 produces on the order of a microsecond-long pulse of electrical current whose total charge is proportional to its light input, i.e., to the light generated by fluorescence in the sample, and, therefore, to the aflatoxin concentration. A PMT was selected for this purpose, given the amount of light expected. It is possible to use other photodetecting transducers such as an avalanche photodiode which while less sensitive than a PMT would be smaller and cheaper.

Figure 4:
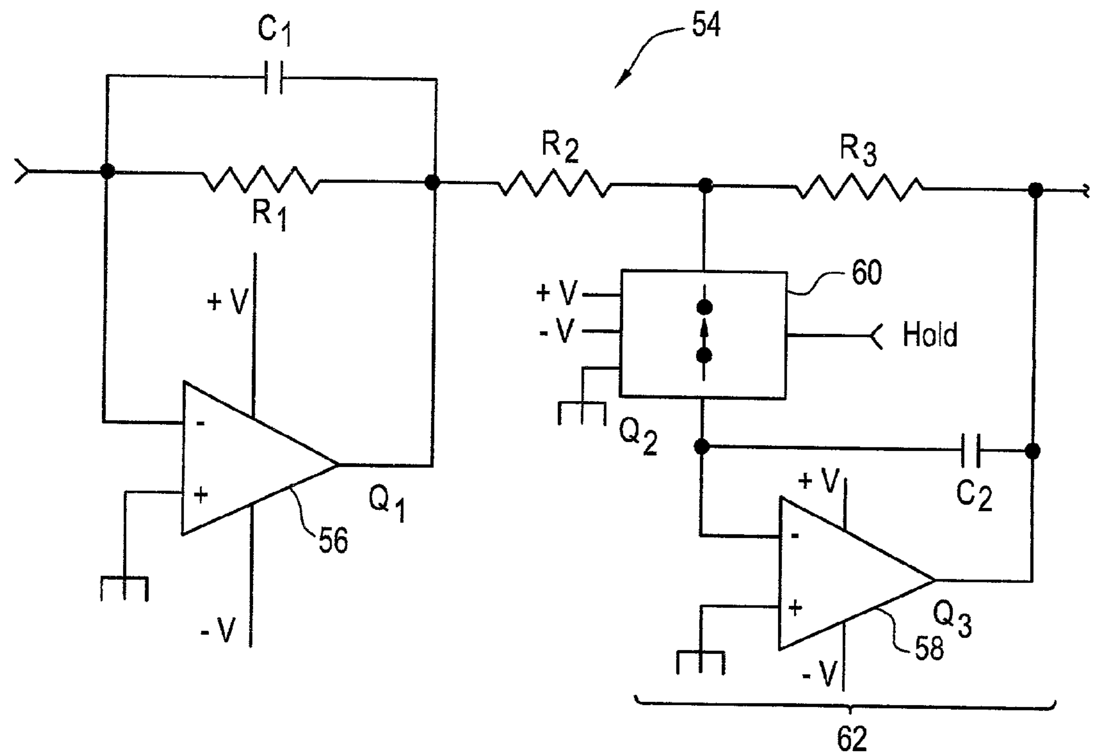
FIG. 4 is a diagram of the receiver circuit in the electro-optical subsystem of FIG. 2.

The PMT's current output is sent to the receiver circuit 54 which is shown schematically in FIG. 2 and in detail in FIG. 4. The PMT output drives a first operational amplifier circuit wired as a transimpedance amplifier 56 with a low pass characteristic that is very long compared to the duration of the light pulse and the duration of the interference of the arc lamp 28 (e.g., 0.1 seconds for the low pass time constant, compared to microsecond-scale durations for the pulse events). The transimpedance amplifier 56 converts the charge (integral of the photocurrent) from the PMT 52 into a decaying exponential pulse with amplitude and area both directly proportional to the charge from the PMT 52.

A second operational amplifier circuit 58 tracks the output of the transimpedance amplifier 56 with another low pass characteristic, such that the output of the transimpedance amplifier 56 is poorly resolved in time at the output of the track/hold circuit 62. The second amplifier 58, together with internal switch 60, forms the track/hold circuit 62 shown in FIG. 4. The track/hold circuit 62 is configured, as discussed below, to hold the value of its output from a time corresponding to the theoretical peak value of the fluorescence-induced pulse. The two-time delays of the receiver circuit 54 resulting from the transimpedance amplifier 56 and the track/hold circuit 62 decouple the final measurement from the large electromagnetic interference generated by the arc lamp 42. The exact timing and lag behaviors of the transimpedance and second amplifiers are optimized, but their values and detailed relationships can be different and the invention will still work.

As shown in FIG. 4, the output of the transimpedance amplifier 56 is input to the track/hold circuit 62 that is configured to provide an output that tracks its input if internal switch 60 is in its normally closed condition. If the switch 60 is placed in the open condition, the track/hold circuit 62 holds the voltage at its output that was present immediately prior to the switch being opened. The track and hold circuit 62 is switched into hold mode at the time that its output amplitude is the maximum in response to a pulse from the PMT 52.

The track/hold circuit 62 reaches a peak response at a time long after a signal pulse comes from the detector 52 and the peak signal comes from the transimpedance amplifier 56. The track/hold circuit 62 is placed in its hold mode also long after the pulse from the arc lamp 42 occurred, and the track/hold circuit's output is directly proportional to the fluorescent light generated. The hold condition is initiated at the time calculated for the peak signal, although other times near that time would provide nearly equivalent results.

Finally, the held output/value, e.g., the fluorescence intensity, is applied to the input to a digitizer/numerical display 64 to be digitized and displayed to the operator of the instrument. The system turns itself off after display and flushing functions are complete.

Flushing of the system is accomplished by pumping the fluid for rinsing (buffer) through the system to wash it free of analyte. A small amount of elution fluid is injected to remove any additional binding analyte. Additional buffer is then used to rinse the system to ensure cleanliness. The external port 16 is opened and the system backflushes to remove any sample from valve 28, in addition to rehydrating the material in the affinity column 34.

The invention is a sensor platform that can be used to detect the presence and measure the amount of many analytes of importance in the areas of environmental or agricultural science, law enforcement, chemical and biological warfare, and clinical medicine and healthcare. A non-inclusive list of potential analytes is:

Environmental/Agricultural Analytes
fumonisins
ochratoxin
deoxynivalenol
zearalenone
pesticides
pfiesteria toxin
polynuclear aromatics
*E. coli* toxin
listeria
Drugs of Abuse
amphetamines cocaine
heroin/morphine
THC
LSD
PCP
Chemical and Biological Warfare Threats
botulism toxin
nerve agents
anthrax
plague
other microbes
Health/Medical Interest
pathogens
metabolites of agents, toxins, threats, etc.
metabolites of therapeutic drugs to set dose.

It will be understood that the invention is not limited to the embodiments described above, it being apparent to those skilled in the art that various changes and modifications can be made without departing from the spirit of the invention or the scope of the appended claim.

We claim:

1. A hand held, self-contained, automatic sensor for detecting and quantifying the amount of an analyte in a sample, the sensor comprising:

power supply;

digital means for automatically controlling the operation of the sensor;

an external port for receiving the sample;

means for driving fluids in the sensor after the sample is received;

means for extracting the analyte from the sample; and means for measuring the fluorescence of the extracted analyte to detect and quantify the amount of analyte in the sample.

2. The sensor as recited in claim 1, further comprising a self-contained module, the module being insertable into and removable from the sensor as a unit, the means for extracting the analyte being located in the module.

3. The sensor as recited in claim 1, further comprising means for providing the analyte with a measurable fluorescence when the analyte does not have a measurable natural fluorescence.

4. The sensor as recited in claim 3, further comprising a self-contained module, the module being insertable into and removable thin the sensor as a unit, the means for extracting the analyte and the means for providing a measurable fluorescence being located in the module.

5. The sensor as recited in claim 1, wherein the means for extracting the analyte comprises an affinity column for binding and concentrating the analyte contained in the sample.

6. The sensor as recited in claim 5, wherein the means for extracting the analyte further comprises:

a first reservoir containing a fluid for rinsing the affinity column clean of any dissolved or suspended material other than the bound analyte; and a second reservoir containing an clution fluid for releasing the analyte from the affinity column.

7. The sensor as recited in claim 6, further comprising a self-contained module, the module being insertable into and removable from the sensor as a unit, the affinity column, the first reservoir and the second reservoir being located in the module.

8. The sensor as recited in claim 6, further comprising means for providing the analyte with a measurable fluorescence when the analyte does not have a measurable natural fluorescence.

9. The sensor as recited in claim 8, the means for providing a measurable fluorescence comprising a third reservoir containing a solution for providing the analyte with a measurable fluorescence, the solution being added to the analyte after the analyte leaves the affinity column.

10. The sensor as recited in claim 9, further comprising a self-contained module, the module being insertable into and removable from the sensor as a unit, the affinity column, the first reservoir, the second reservoir and the third reservoir being located in the module.

11. The sensor as recited in claim 9, wherein the solution comprises a developer for derivatizing the analyte to create a fluorescent tag.

12. The sensor as recited in claim 9, wherein the solution comprises a fluorescent tagged compound.

13. The sensor as recited in claim 9, further comprising means for mixing the solution and the analyte before the analyte enters the means for measuring the fluorescence.

14. The sensor as recited in claim 9, further comprising a self-contained module, the module being insertable into and removable from the sensor as a unit, the first reservoir, the second reservoir and the third reservoir being located in the module.

15. The sensor as recited in claim 6, further comprising a self-contained module, the module being insertable into and removable from the sensor as a unit, the first reservoir and the second reservoir being located in the module.

16. The sensor as recited in claim 6, further comprising a waste chamber for receiving the fluid for rinsing, the elution fluid, the analyte, and a solution used for washing the sensor after use.

17. The sensor as recited in claim 16, further comprising a self-contained module, the module being insertable into and removable from the sensor as a unit, the first reservoir, the second reservoir and the waste chamber being located in the module.

18. The sensor as recited in claims 1, 3, 6 or 8, the means for measuring the fluorescence comprising:

a fluorometric cell for receiving the analyte to be detected;

means for illuminating the fluorometric cele with radiation;

a first optical system for collecting the radiation from the illuminating means and focusing the radiation on the fluorometric cell and the analyte therein, a first filter positioned between the first optical system and the fluorometric cell for removing radiation received from the first optical system except primarily radiation within a specific band that excites fluorescence associated with the analyte thereby causing the analyte to emit a fluorescent light in the fluorometric cell;

a second optical system for collecting the radiation including the fluorescent light emitted by the analyte leaving the fluormetric cell and focusing the fluorescent light on a detector;

a second filter for passing only the fluorescent light emitted by the analyte; and the detector for converting the fluorescent light emitted by the analyte into electrical current, the total charge of the current being proportional to the amount of fluorescent light that is input to the detector and to the concentration of the analyte in the sample.

19. The sensor as recited in claim 18, the means for measuring the fluorescence further comprising:

means for digitizing the charge of the current; and means for displaying the charge of the current.

20. The sensor as recited in claim 18, further comprising a waste chamber for receiving the fluid for rinsing, the elution fluid and the analyte used to detect and quantify the amount of analyte in the sample, and for also receiving a solution used for washing the sensor after use.

21. The sensor as recited in claim 18, wherein the means for driving fluids comprises a peristaltic pump.

22. The sensor as recited in claim 18, wherein the fluorometric cell comprises a cuvette.

23. The sensor as recited in claim 18, wherein the means for illuminating comprises an arc lamp.

24. The sensor as recited in claim 18, wherein the detector comprises a photomultiplier tube.

25. The sensor as recited in claim 18, the means for measuring the fluorescence further comprising:

a first operational amplifier circuit having a low pass characteristic for receiving the charge of the current from the detector and converting the charge of the current into a pulse;

a circuit for tracking the output of the first operational amplifier, the circuit having a low pass characteristic, and for holding a value that is a maximum in response to the charge of the current received from the detector; and means for digitizing and displaying the held value.

26. The sensor as recited in claim 25, the circuit for tracking and holding comprising:

a second operational amplifier circuit having a low pass characteristic; and a switch, the switch when open holding the value that is the maximum in response to the charge of the current received from the detector and when closed sending the held value to the digitizing and displaying means.

27. The sensor as recited in claim 26, the first operational amplifier circuit comprising a transimpedance amplifier.

28. A sensor for detecting and quantifying the amount of an analyte in a sample, the sensor comprising:

a hand held, enclosed container;

a power supply;

digital means for automatically controlling the operation of the sensor;

an external port in the container for receiving the sample;

means for driving fluids in the sensor after the sample is received;

means for extracting the analyte from the sample; and means for measuring the fluorescence of the extracted analyte to detect and quantify the amount of analyte in the sample, the power supply, the digital means, the means for driving fluids, the means for extracting the analyte and the means for measuring the fluorescence being located in the container.

29. The sensor as recited in claim 28, further comprising means for providing the analyte with a measurable fluorescence when the analyte does not have a measurable natural fluorescence, the means for providing a measurable fluorescence being located in the container.

30. The sensor as recited in claim 28, wherein the means for extracting the analyte comprises an affinity column for binding and concentrating the analyte contained in the sample.

31. The sensor as recited in claim 30, wherein the means for extracting the analyte further comprises:

a first reservoir containing a fluid for rinsing the affinity column clean of any dissolved or suspended material other than the bound analyte; and a second reservoir containing an elution fluid for releasing the analyte from the affinity column.

32. The sensor as recited in claim 31, the means for measuring the fluorescence comprising:

a fluorometric cell for receiving the analyte to be detected;

means for illuminating the fluorometric cell with radiation;

a first optical system for collecting the radiation from the illuminating means and focusing the radiation on the fluorometric cell and the analyte therein;

a first filter positioned between the first optical system and the fluorometric cell for removing radiation received from the first optical system except primarily radiation within a specific band that excites fluorescence associated with the analyte thereby causing the analyte to emit a fluorescent light in the fluorometric cell;

a second optical system for collecting the radiation including the fluorescent light emitted by the analyte leaving the fluorometric cell and focusing the fluorescent light on a detector;

a second filter for passing only the fluorescent light emitted by the analyte; and a detector for converting the fluorescent light emitted by the analyte into electrical current, the total charge of the current being proportional to the amount of fluorescent light that is input to the detector and to the concentration of the analyte in the sample.

33. The sensor as recited in claim 32, the means for measuring the fluorescence further comprising:

means for digitizing the charge of the current; and means for displaying the charge of the current.

34. The sensor as recited in claim 32, the means for measuring the fluorescence further comprising:

means for providing the analyte with a measurable fluorescence when the analyte does not have a measurable natural fluorescence, the means for providing a measurable fluorescence being located in the container;

a first operational amplifier circuit having a low pass characteristic for converting the electrical current from the detector into a pulse;

a circuit for tracking the output of the first operational amplifier and for holding a value that is the maximum in response to the pulse, the circuit comprising:

a second operational amplifier circuit having a low pass characteristic;

a switch, the switch when open holding the value that is the maximum in response to the pulse and when closed sending the held value to the digitizing and displaying means; and means for digitizing and displaying the held value.

* * * * *

UNITED STATES PATENT AND TRADEMARK OFFICE

CERTIFICATE OF CORRECTION

PATENT NO. : 6,969,605 B2
DATED : November 29, 2005
INVENTOR(S) : Anderson et al.

It is certified that error appears in the above-identified patent and that said Letters Patent is hereby corrected as shown below:

Column 9,
Line 41, delete "thin" and insert -- from --.
Line 57, delete "clution" and insert -- elution --.

Signed and Sealed this

Twenty-first Day of February, 2006

JON W. DUDAS
*Director of the United States Patent and Trademark Office*